United States Patent
Berthier et al.

(10) Patent No.: US 10,376,890 B2
(45) Date of Patent: Aug. 13, 2019

(54) APPARATUS, SYSTEMS AND METHODS FOR MODULAR MICROFLUIDIC DEVICES

(71) Applicant: Stacks to the Future LLC, Monona, WI (US)

(72) Inventors: Erwin Berthier, Seattle, WA (US); Theodorus de Groot, Madison, WI (US); Jiaquan Yu, Madison, WI (US); Ashleigh Theberge, Seattle, WA (US); David Beebe, Monona, WI (US)

(73) Assignee: Stacks to the Future LLC, Monona, WI (US)

(*) Notice: Subject to any disclaimer, the term of this patent is extended or adjusted under 35 U.S.C. 154(b) by 128 days.

(21) Appl. No.: 15/425,720

(22) Filed: Feb. 6, 2017

(65) Prior Publication Data
US 2017/0239661 A1  Aug. 24, 2017

Related U.S. Application Data

(60) Provisional application No. 62/291,077, filed on Feb. 4, 2016.

(51) Int. Cl.
*B01L 3/00* (2006.01)
*B81B 7/00* (2006.01)
(Continued)

(52) U.S. Cl.
CPC .......... *B01L 3/5635* (2013.01); *B01L 3/5027* (2013.01); *B01L 3/50273* (2013.01);
(Continued)

(58) Field of Classification Search
CPC ..... B01L 2300/0672; B01L 2300/0816; B01L 2400/0406; B01L 2400/086; B01L 2200/027; B01L 2200/0621; B01L 2200/0684; B01L 2300/044; B01L 2300/047; B01L 2300/0861;
(Continued)

(56) References Cited

U.S. PATENT DOCUMENTS 6,908,594 B1 * 6/2005 Schaevitz ............. B01L 3/5025
                                                        204/451
8,389,294 B2 3/2013 Beebe et al.
(Continued)

OTHER PUBLICATIONS

Puccinelli et al., "Automated high-throughput microchannel assays for cel biology: operational optimization and characterization", Feb. 1, 2010, pp. 25-32, vol. 15, No. 1, Publisher: JALA Charlottesv VA.
(Continued)

*Primary Examiner* — Jennifer Wecker
(74) *Attorney, Agent, or Firm* — Davis, Brown, Koehn, Shors & Roberts, P.C.; Matthew Warner-Blankenship

(57) ABSTRACT

The disclosed apparatus, systems and methods relate to a modular microfluidic device, the component comprising a channel comprising an apex opening, wherein the apex opening that is at least partially surrounded by a collar configured to pin a liquid within the channel. The modular microfluidic device may also have a structural tip in or near the apex opening which is configured to allow for the flow of the liquid into the channel from a second component for a modular microfluidic device when the component is engaged with the second component.

18 Claims, 10 Drawing Sheets

(51) Int. Cl.
G01N 33/50 (2006.01)
C12M 3/06 (2006.01)

(52) U.S. Cl.
CPC ......... *B01L 3/50857* (2013.01); *B01L 3/5023* (2013.01); *B01L 3/502715* (2013.01); *B01L 3/502738* (2013.01); *B01L 2200/027* (2013.01); *B01L 2200/028* (2013.01); *B01L 2200/0621* (2013.01); *B01L 2200/0684* (2013.01); *B01L 2300/0861* (2013.01); *B01L 2300/0867* (2013.01); *B01L 2300/161* (2013.01); *B01L 2400/0406* (2013.01); *C12M 23/16* (2013.01)

(58) Field of Classification Search
CPC ....... B01L 2300/0867; B01L 2300/161; B01L 2400/0481; B01L 2400/0677; B01L 2400/0683; B01L 2400/0688; B01L 3/5023; B01L 3/5027; B01L 3/502715; B01L 3/502723; B01L 3/50273; B01L 3/502738; B01L 3/50853; C12M 23/16
See application file for complete search history.

(56) References Cited

U.S. PATENT DOCUMENTS 9,186,670 B2  11/2015  Berthier et al.
9,289,763 B2  3/2016  Berthier et al.
2007/0243523 A1*  10/2007  Ionescu-Zanetti ........... B01L 3/502738 435/4
2014/0038306 A1*  2/2014  Berthier ............. B01L 3/50273 436/172
2016/0102281 A1*  4/2016  Moritz ................... C12M 25/01 435/353

OTHER PUBLICATIONS

Domenech et al., "Cellular observations enabled by microculture paracrine signaling and population demographics", "Integr Bil", Mar. 1, 2009, pp. 267-274, vol. 3.
Guckenberger et al., "High Density self contained microfluidic KOALA kits for use by everyone", Apr. 20, 2015, pp. 146-153, vol. 2, Publisher: PubMed.
Warrick, "High thorughput micorfluidics improved sample treatment and washing over standard wells", "Lab Chip", 1/1/207, pp. 316-321, vol. 7.
Berthier et al., "Kit-On-A-Lid-Assays for accessible self-contained cell assays", "Lab Chip", Feb. 7, 2013, pp. 424-431, vol. 13, No. 3, Publisher: PubMed.
Blagovic et al., "Microfluidic perfusion for regulating diffusible signaling in stem cells,", Jan. 1, 2011, vol. 6, No. 8, Publisher: PLoS One.
Sackmann, "Microfluidic kit-on-a-lid: a versatile plafform for neutrophil chematoaxis assays", "Blood", Oct. 4, 2014, pp. e45-e53, vol. 120, No. 14, Publisher: PubMed.
Walker et al., "A passive pumping method for microfluidic devices", "Lab Chip", Jan. 2010, pp. 131-134, vol. 2.
Casavant, "Suspended Mlcrofluidics", Jun. 18, 2013, vol. 110, No. 25, Publisher: PNAS.

* cited by examiner

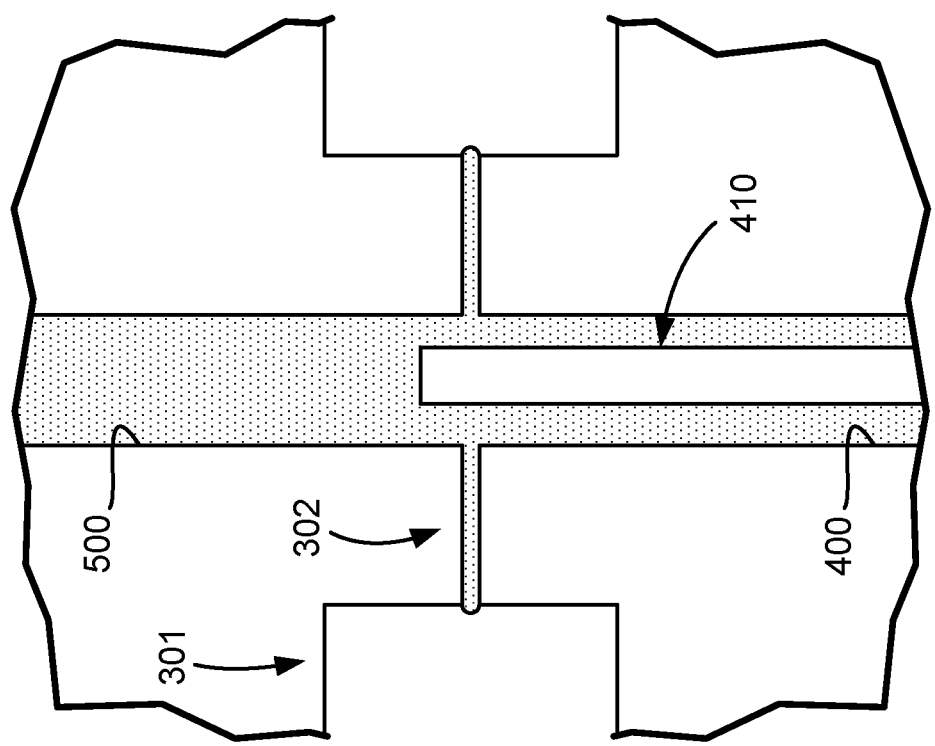

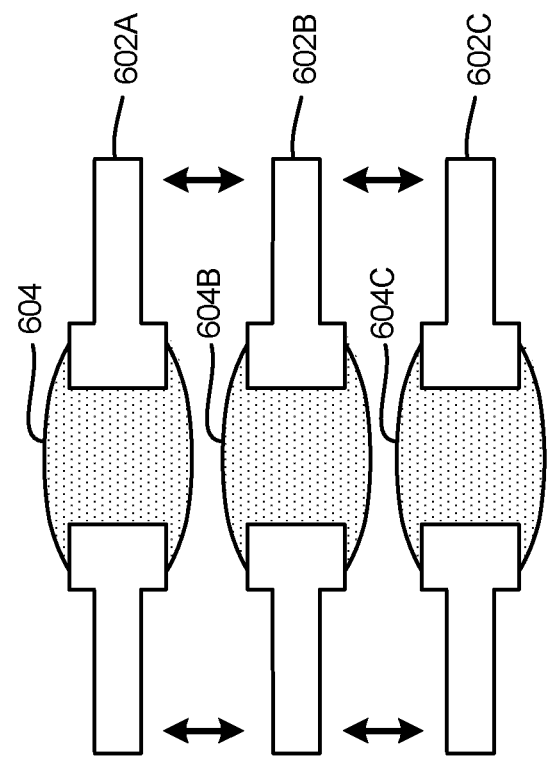
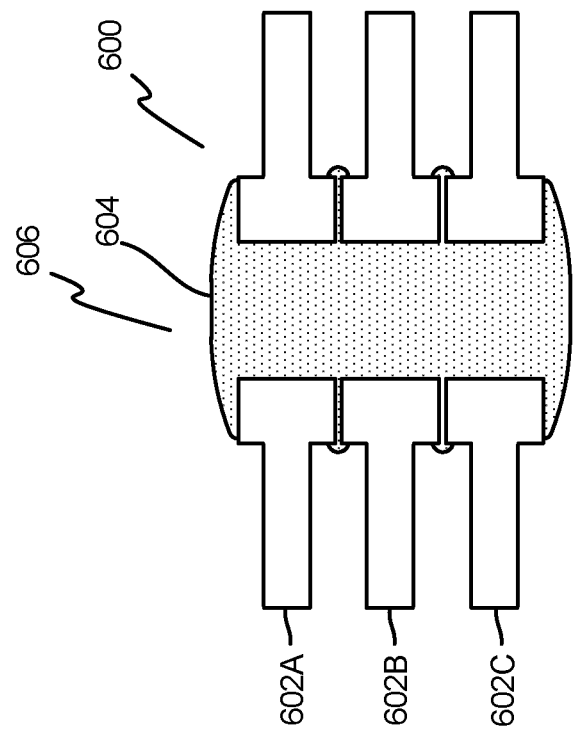
FIG. 6A
FIG. 6B

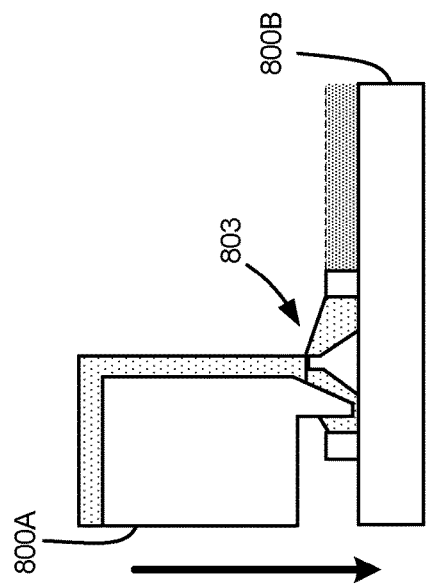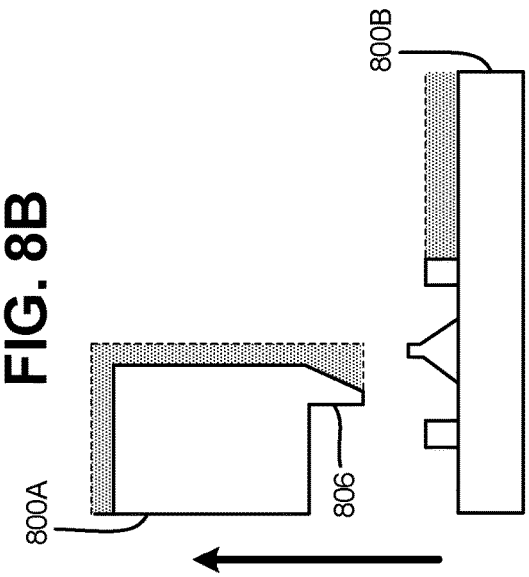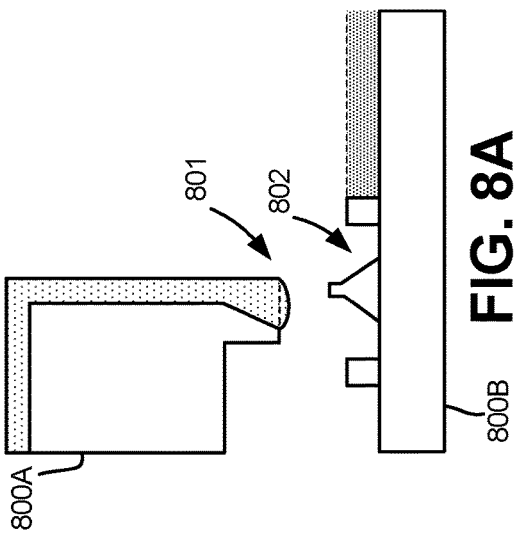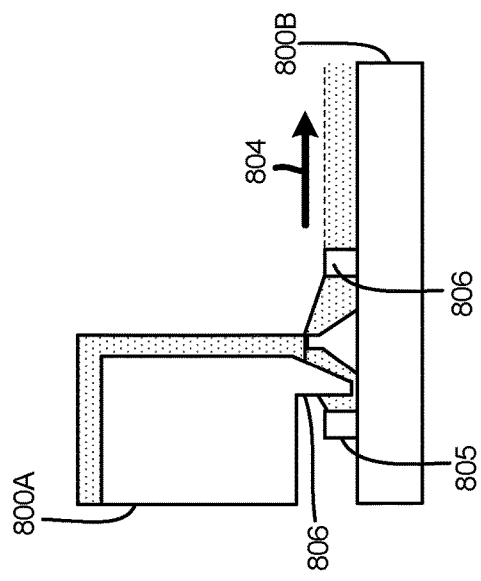

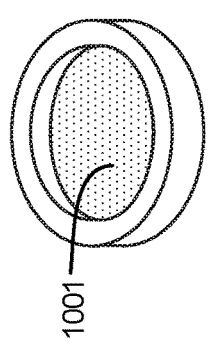
Fig. 10A
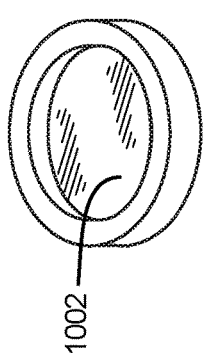
Fig. 10B
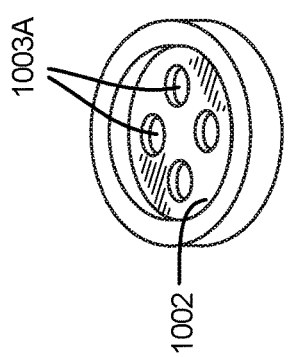
Fig. 10C
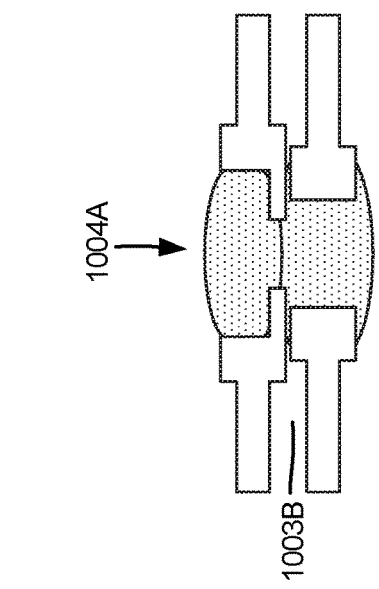
Fig. 10D
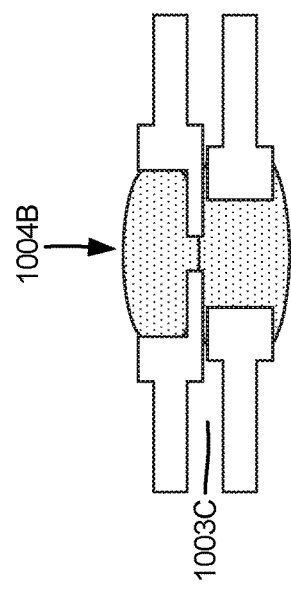
Fig. 10E
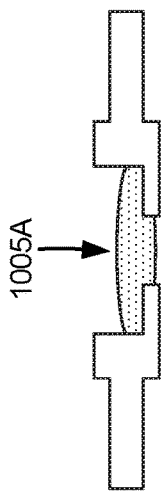
Fig. 10F
Fig. 10G
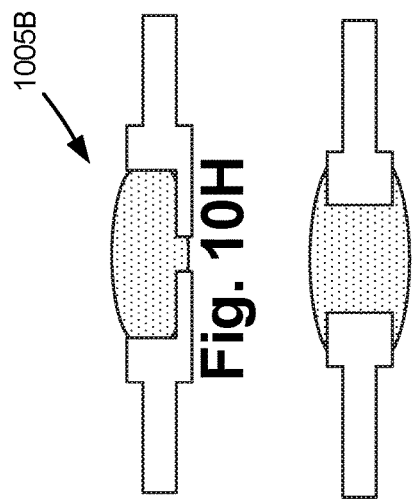
Fig. 10H
Fig. 10I

APPARATUS, SYSTEMS AND METHODS FOR MODULAR MICROFLUIDIC DEVICES

CROSS-REFERENCE TO RELATED APPLICATION(S)

This application claims priority to U.S. Provisional Application No. 62/291,077 filed Feb. 4, 2016 and entitled "Modular Microfluidic Devices," which is hereby incorporated by reference in its entirety under 35 U.S.C. § 119(e).

STATEMENT OF GOVERNMENT INTEREST

This work was supported in part by NIH CA155192, NIHDK100022. The government has certain rights in this invention.

TECHNICAL FIELD

The disclosed technology relates generally to microfluidic devices. More particularly, provided herein are modular microfluidic devices.

BACKGROUND

Microfluidic methods improve on many traditional in vitro assays for the studying of soluble factor interactions in multicultural systems, the interaction between cells and their substrate, and properties of cell migration. Furthermore, microfluidic methods improve various aspects of fluid handling including the control of fluid paths, washing efficiency, and reagent use. While the highest degree of precision is achievable with syringe-based microfluidics, the equipment and skill required represent a barrier to adoption in biology laboratories. An increasing body of work has identified this issue and developed more accessible open microfluidic platforms.

Previous inventions have disclosed open microfluidic devices which use capillary flow as opposed to pressurized force through use of. These devices have been cannot deal with particular problem of the device being able to be reconfigurable. As a result, there exists a need for new modular microfluidic devices that are capable of being reconfigured for rapid assay prototyping and development.

BRIEF SUMMARY

Provided herein are components for modular microfluidic devices, the components comprising a channel comprising an apex opening, wherein the apex opening is at least partially surrounded by a collar configured to pin a liquid within the channel. Another aspect of the invention are components for modular microfluidic devices, the components comprising a collar at least partially surrounding an apex opening of a channel, wherein the collar is configured to pin a liquid within the channel.

In some embodiments, the collar comprises a channel sidewall, a face, and an outer sidewall, wherein the channel sidewall and the face define a first collar angle and wherein the face and the outer sidewall define a second collar angle. In some embodiments, the collar comprises a collar material. In some embodiments, the first angle is greater than the contact angle of the liquid disposed on the collar material. In some embodiments, the second angle is greater than the contact angle of the liquid disposed on the collar material.

In some embodiments, the channel has a length greater than 1 mm and up to 100 mm. In some embodiments, the channel has a mean radius of about 100 um to about 3 mm. In some embodiments, the channel has a channel volume of about 0.1 uL to about 300 uL. In some embodiments, the channel is a closed channel. In other embodiments, the channel is an open channel. In some embodiments, the collar has a width of about 100 um to about 2 mm.

In some embodiments, the collar is configured to allow for flow of the liquid within the channel to a second component for a modular microfluidic device when the component is engaged with the second component; the collar is configured to allow for diffusion of the liquid within the channel to a second component for a modular microfluidic device when the component is engaged with the second component; or both. In some embodiments, the second component comprises a second channel comprising a second apex opening, wherein the second apex opening is at least partially surrounded by a second collar configured to pin a second liquid within the channel. In some embodiments, the liquid within the channel suspends cells, the second liquid within the second channel suspends cells, or both.

Also provided herein are components for a modular microfluidic device, the component comprising a channel comprising an apex opening and a structural tip in or near the apex opening, wherein the apex opening is at least partially surrounded by a collar configured to pin a liquid within the channel and wherein the pin is configured to allow for the flow of the liquid into the channel from a second component for a modular microfluidic device when the component is engaged with the second component.

Also provided herein are components for a modular microfluidic device, the components comprising a channel comprising a first apex opening and a second apex opening, wherein the first apex opening is at least partially surrounded by a first collar configured to pin a liquid within the channel and wherein the second apex opening is at least partially surrounded by a second collar configured to pin a liquid within the channel.

Also provided herein are components for a modular microfluidic device, the component comprising a channel comprising a first apex opening and a first pin at or near the first apex opening, wherein the first apex opening is at least partially surrounded by a first collar configured to pin a liquid within the channel and wherein the first pin is configured to allow for the flow of the liquid into the channel from a second component for a modular microfluidic device when the component is engaged with the second component, and a second apex opening, wherein the second apex opening is at least partially surrounded by a second collar configured to pin a liquid within the channel.

Also provided herein are components for a modular microfluidic device, the components comprising a channel comprising (a) a first apex opening and a first pin at or near the first apex opening, wherein the first apex opening is at least partially surrounded by a first collar configured to pin a liquid within the channel and wherein the first pin is configured to allow for the flow of the liquid into the channel from a second component for a modular microfluidic device when the component is engaged with the second component, and (b) a second apex opening and a second pin at or near the second apex opening, wherein the second apex opening is at least partially surrounded by a second collar configured to pin a liquid within the channel and wherein the second pin is configured to allow for the flow of the liquid into the channel from a third component for a modular microfluidic device when the component is engaged with the third component.

Also provided herein are modular microfluidic devices.

One general aspect includes A component for a modular microfluidic device, the component including a channel including an apex opening, where the apex opening is at least partially surrounded by a collar configured to pin a liquid within the channel. Implementations may include one or more of the following features. The component, where the collar includes a channel sidewall, a face, and an outer sidewall, where the channel sidewall and the face define a first collar angle and where the face and the outer sidewall define a second collar angle. The component of any of the embodiments previously described, where the collar includes a collar material. The component of any of the embodiments previously described, where the first angle is greater than the contact angle of the liquid disposed on the collar material. The component of any of the embodiments previously described, where the second angle is greater than the contact angle of the liquid disposed on the collar material. The component of any of the embodiments previously described, where the channel has a channel length of about 1 mm to about 100 mm. The component of any of the embodiments previously described, where the channel has a mean radius of about 100 µm to about 2 mm. The component of any of the embodiments previously described, where the channel has a channel volume of about 100 nL to about 300 L. The component of any of the embodiments previously described, where the channel is a closed channel or an open channel. The component of any of the embodiments previously described, where the collar has a width of about 100 m to about 2 mm. The component of any of the embodiments previously described, where (i) the collar is configured to allow for flow of the liquid within the channel to a second component for a modular microfluidic device when the component is engaged with the second component; (ii) the collar is configured to allow for diffusion of the liquid within the channel to a second component for a modular microfluidic device when the component is engaged with the second component; or (iii) both (i) and (ii). The component of any of the embodiments previously described, where the second component includes a second channel including a second apex opening, where the second apex opening is at least partially surrounded by a second collar configured to pin a second liquid within the channel. The component of any of the embodiments previously described, where (i) the liquid within the channel suspends cells, (ii) the second liquid within the second channel suspends cells, or both (i) and (ii). A modular microfluidic device, the modular microfluidic device including a member selected from the group including of the component the component the component the component the component and combinations thereof. A modular microfluidic device, the modular microfluidic device including at least two members selected from the group including of the component the component the component the component and the component. The component where the collar includes a channel sidewall, a face, and an outer sidewall, where the channel sidewall and the face define a first collar angle and where the face and the outer sidewall define a second collar angle.

One general aspect includes A component for a modular microfluidic device, the component including a collar at least partially surrounding the apex opening of a channel, where the collar is configured to pin a liquid within the channel.

One general aspect includes A component for a modular microfluidic device, the component including (a) a channel including an apex opening and (b) a structural tip in or near the apex opening, where the apex opening is at least partially surrounded by a collar configured to pin a liquid within the channel and where the pin is configured to allow for the flow of the liquid into the channel from a second component for a modular microfluidic device when the component is engaged with the second component.

Implementations may include one or more of the following features. The component where the collar includes a channel sidewall, a face, and an outer sidewall, where the channel sidewall and the face define a first collar angle and where the face and the outer sidewall define a second collar angle.

One general aspect includes the component of any of the embodiments previously described, where the collar includes a collar material.

One general aspect includes the component of any of the embodiments previously described, where the first angle is greater than the contact angle of the liquid disposed on the collar material.

One general aspect includes the component of any of the embodiments previously described, where the second angle is greater than the contact angle of the liquid disposed on the collar material.

One general aspect includes the component of any of the embodiments previously described, where the channel has a channel length of about 1 mm to about 100 mm.

One general aspect includes the component of any of the embodiments previously described, where the channel has a mean radius of about 100 µm to about 2 mm.

One general aspect includes the component of any of the embodiments previously described, where the channel has a channel volume of about 100 nL to about 300 L.

One general aspect includes the component of any of the embodiments previously described, where the channel is a closed channel or an open channel.

One general aspect includes the component of any of the embodiments previously described, where the collar has a width of about 100 µm to about 2 mm.

One general aspect includes the component of any of the embodiments previously described, where the collar is configured to allow for flow of the liquid within the channel to a second component for a modular microfluidic device when the component is engaged with the second component.

One general aspect includes the component of any of the embodiments previously described, where (i) the liquid within the channel suspends cells, (ii) the second liquid within the second channel suspends cells, or both (i) and (ii).

One general aspect includes a component for a modular microfluidic device, the component including a channel including a first apex opening and a second apex opening, where the first apex opening is at least partially surrounded by a first collar configured to pin a liquid within the channel and where the second apex opening is at least partially surrounded by a second collar configured to pin a liquid within the channel.

One general aspect includes A component for a modular microfluidic device, the component including a channel including (a) a first apex opening and a first pin at or near the first apex opening, where the first apex opening is at least partially surrounded by a first collar configured to pin a liquid within the channel and where the first pin is configured to allow for the flow of the liquid into the channel from a second component for a modular microfluidic device when the component is engaged with the second component, and (b) a second apex opening, where the second apex opening is at least partially surrounded by a second collar configured to pin a liquid within the channel.

One general aspect includes A component for a modular microfluidic device, the component including a channel including (a) a first apex opening and a first pin at or near the first apex opening, where the first apex opening is at least partially surrounded by a first collar configured to pin a liquid within the channel, and where the first pin is configured to allow for the flow of the liquid into the channel from a second component for a modular microfluidic device when the component is engaged with the second component; and (b) a second apex opening and a second pin at or near the second apex opening, where the second apex opening is at least partially surrounded by a second collar configured to pin a liquid within the channel, and where the second pin is configured to allow for the flow of the liquid into the channel from a third component for a modular microfluidic device when the component is engaged with the third component.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 5 is a cross-sectional view of an exemplary pinning component within parts of modular microfluidic devices in liquid communication, according to an exemplary embodiment.

FIG. 6A is a cross-sectional view of stacks of devices with multiple layers, according to exemplary embodiments.

FIG. 6B is a cross-sectional view of stacks of devices with multiple layers, according to alternate embodiments.

FIG. 8A is a side view showing one example of flow between modular devices, according to exemplary implementations.

FIG. 8B is a further side view showing one example of flow between modular devices, according to the implementation of FIG. 8A.

FIG. 8C is a further side view showing one example of flow between modular devices, according to the implementation of FIG. 8A.

FIG. 8D is a further side view showing one example of flow between modular devices, according to the implementation of FIG. 8A.

FIG. 10A is a perspective view of a suspended chamber used to contain liquid or hydrogel, according to one embodiment.

FIG. 10B is a perspective view of a layer with a solid bottom preventing vertical liquid connection, according to one embodiment.

FIG. 10C is a perspective view of a layer with a solid bottom having pores, according to yet another embodiment.

FIG. 10D is a cross-sectional side view depicting a liquid exchange process controlled by the size of pore, according to one embodiment.

FIG. 10E is a cross-sectional side view depicting a liquid exchange process controlled by the size of pore, according to one embodiment.

FIG. 10F is a cross-sectional side view depicting a liquid exchange process controlled by the size of pore, according to one embodiment.

FIG. 10G is a cross-sectional side view depicting a liquid exchange process controlled by the size of pore, according to one embodiment.

FIG. 10H is a cross-sectional side view depicting a liquid exchange process controlled by the size of pore, according to one embodiment.

FIG. 10I is a cross-sectional side view depicting a liquid exchange process controlled by the size of pore, according to one embodiment.

DETAILED DESCRIPTION

Figure 1:
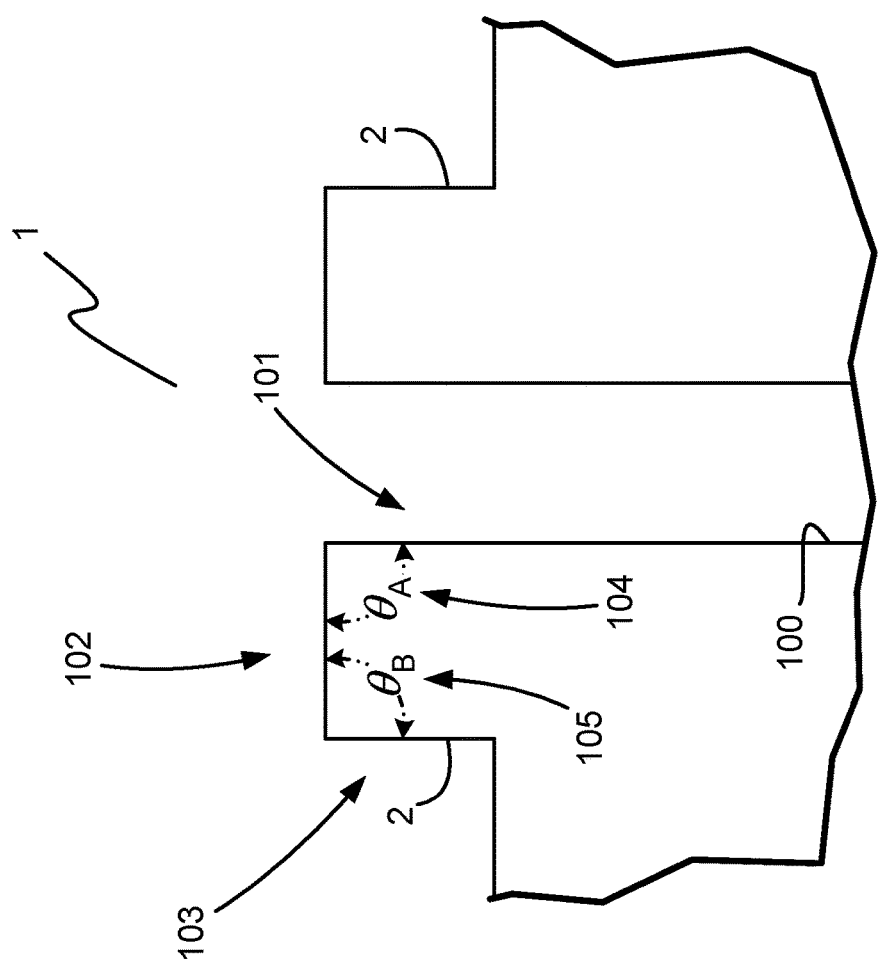
FIG. 1 is a cross-sectional view of part of a modular microfluidic device, according to an exemplary embodiment.

The various embodiments disclosed or contemplated herein relate to modular component open microfluidic platforms, as is described further herein.

Open and suspended microfluidic techniques allow the creation of micro scale platforms devoid of channel floor, ceiling, or other interfaces. A significant benefit of the openness of these systems is the ability to access any point of the fluid flow at any time during the operation of the devices. Previous devices have been unable to be accessed and reconfigured during operation. This high level of accessibility of our device enables a plethora of significant applications for biological and clinical studies, specifically in the operation of functional cell-based systems that require multiple steps of preparation or readout.

The present disclosure demonstrates the potential of these systems through the development of modular component open microfluidic platforms that allow fluidic connection between the multiple components and exchange of fluids or cells. In some embodiments, the modular components are block systems that allow universal assembly of interlocking devices. These connections rely on a protrusion, or structural tip, in the receiving device that extends into the fluidic path of the donor component. When connected this setup creates a capillary path from one modular device to the other. Various implementations place these connecting features on the modified fluidic-devices such that the devices can be assembled in any orientation without creating interference allowing a large degree of modularity. These devices can be utilized as fluidic breadboards allowing the simple development of microfluidic systems that integrate a number of different function features, including, but not limited to, Y-channels, fluid sources, sinks, and mixers.

An interesting aspect of utilizing capillary forces to drive fluid flows is the potential for re-configuring the system during operation. When a modular device is removed from a set of multiple devices, surface tension forces stop the flow of fluid and the flow paths are re-oriented. Various implementations extend the modular open-microfluidic systems to create re-configurable functional cell-based assays. These platforms enable biological or clinical studies, which require controlled interaction between multiple components, such as co-culture interactions.

In various implementations, at a pre-determined point in the protocol, the devices can be assembled and interactions are triggered. Similarly, it is possible to interrupt the interactions by disassembling the devices. In addition to fluid convection and soluble signal diffusion, re-configurable micro-systems are useful to exchange cells. We developed platforms in which 3D matrices can be placed in contact between multiple device components. Cells migrating through the matrix can migrate between the multiple device components. When the blocks are disassembled highly migrating cells remain on the second device component and can be utilized for further analysis.

Unlike most microfluidic tissue culture platforms, the modular microfluidic components herein described require no bonding of layers, facilitating the modularity of the platform and drastically reducing the cost and complexity of fabrication. Simple fabrication enables new stacks devices to be used in lab just hours after design using CNC milling, while simple design and relatively large feature size opens stacks to low-cost, high-throughput injection molding fabrication. This device allows a modular tissue culture platform that incorporates the precision and utility of micro culture device with the ease of use of a well plate, combined with low-cost fabrication, it is an ideal candidate for commercialization. There are many ways to prepare these devices including 3D printing or injection molding. Plastics are the preferred material for the device because they can be injection molded or 3D-printed but a variety of different materials such as glass, wood or metal could be used.

Components for modular microfluidic devices described above comprise a channel comprising an apex opening (as shown, for example at 901 in FIG. 9A), wherein the apex opening is at least partially surrounded by a collar configured to pin a liquid within the channel. In another embodiment, the components for modular microfluidic devices comprise a collar at least partially surrounding the apex opening of a channel, wherein the collar is configured to pin a liquid within the channel. The collar may comprise a channel sidewall, a face, and an outer sidewall, wherein the channel sidewall and the face define a first collar angle and wherein the face and the outer sidewall define a second collar angle.

The collar may comprise any suitable a collar material that allows for the pinning of a liquid within the component. The first angle may be greater than the contact angle of the liquid disposed on the collar material. The second angle is greater than the contact angle of the liquid disposed on the collar material.

The channel may be any suitable length for a particular application. In some embodiments, the channel length may have a length about 1 mm to about 100 mm.

The channel radius may be any suitable radius for a particular application. In some embodiments, the channel may have a mean radius of about 100 um to about 2 mm.

The channel may have any suitable volume for a particular application. In some embodiments, the channel may have a volume of about 100 nL to about 300 uL.

In some embodiments, the channel may be a closed channel. In other embodiments, the channel is an open channel.

The collar may have any suitable radium for a particular application. In some embodiments, wherein the collar has a width of about 100 um to about 2 mm between the channel sidewall and the outer sidewall.

FIG. 1 partially illustrates a component 100 for use with a modular microfluidic device. The collar 2 generally extends the channel 1 away from the surface of the component 100 and allows for the pinning of liquid within the component when the component is isolated from other components. The collar 2 comprises a channel sidewall 101, a face 102, and an outer sidewall 103. The channel sidewall 101 and the face 102 define a first angle 104 ($\theta_A$). The face 102 and the outer sidewall 103 define a second angle 105 ($\theta_B$).

Figure 2:
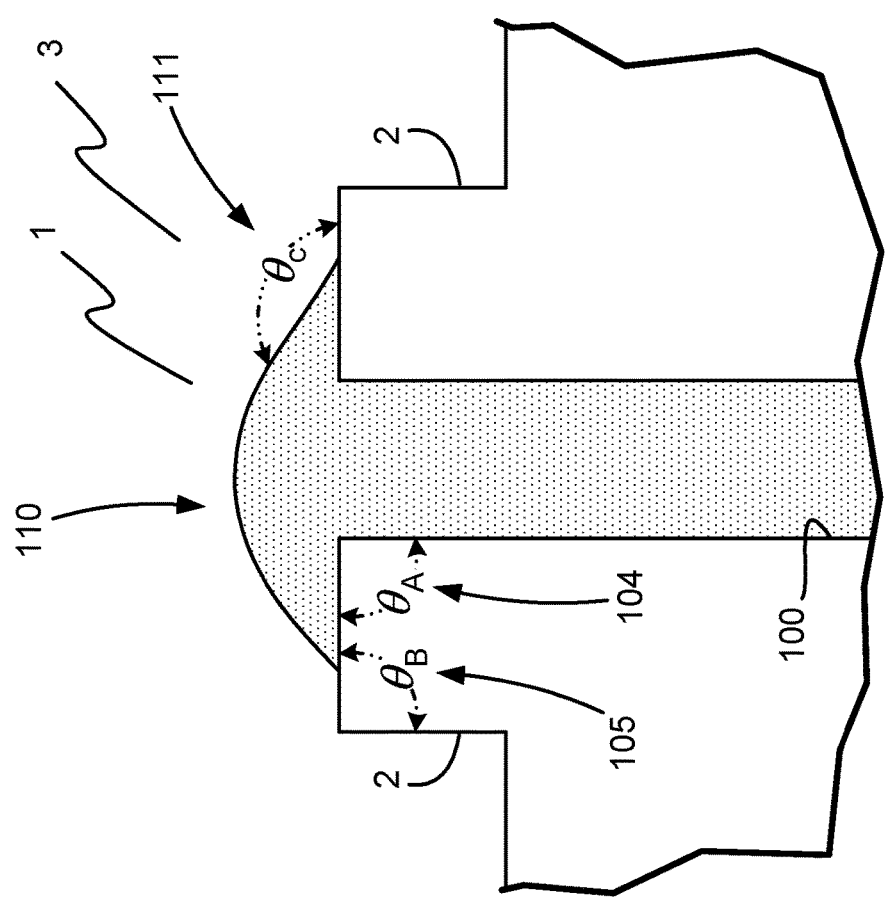
FIG. 2 is a further cross-sectional view of part of a modular microfluidic device, containing liquid, according to an exemplary embodiment.

FIG. 2 partially illustrates component 100 with a liquid 110 pinned within the channel. Although pinning of the liquid 110 may be completely within the channel, it is possible that the liquid 110 will completely or partially wet the face 102 of the collar. The contact angle ($\theta_A$) 111 between the liquid 110 and the face 102 will depend on the surface tension of the liquid 110 and the wettability of the collar material.

In some embodiments, the collar is configured to allow for flow of the liquid within the channel to a second component for a modular microfluidic device when the component is engaged with the second component. In some embodiments, the collar is configured to allow for diffusion of the liquid within the channel to a second component for a modular microfluidic device when the component is engaged with the second component. In some embodiments, the collar is configured to allow for flow and configured to allow from diffusion when the component is engaged with a second component. In certain implementations, the channel 1 comprises an apex opening 3, meaning an opening into the channel 1 surrounding the collar 2. On such implementation is best shown in FIG. 9A at 901.

In some embodiments, the second component comprises a second channel comprising a second apex opening, wherein the second apex opening is at least partially surrounded by a second collar configured to pin a second liquid within the channel.

Figure 3B:
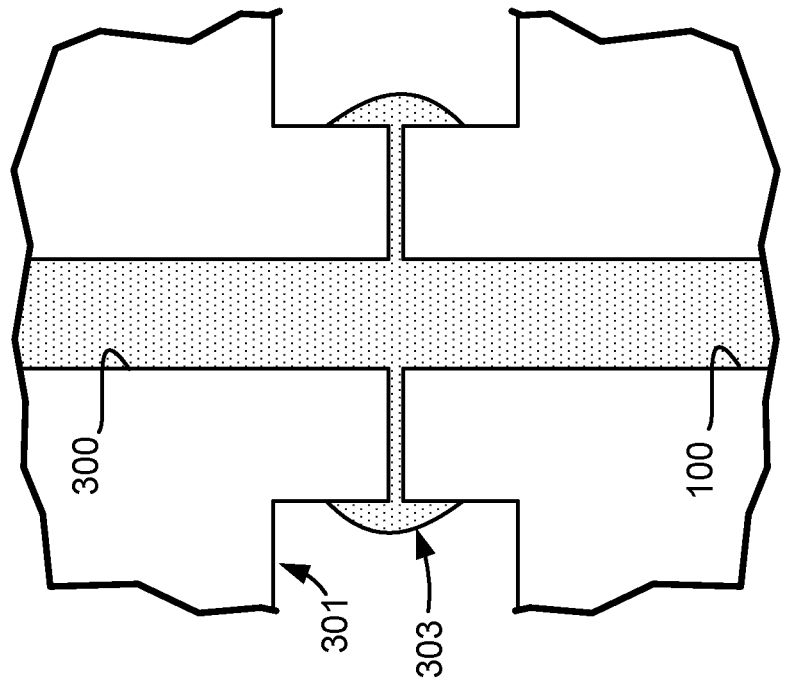
FIG. 3B is a further cross-sectional view of a modular microfluidic device in liquid communication, according to an exemplary embodiment.
Figure 3A:
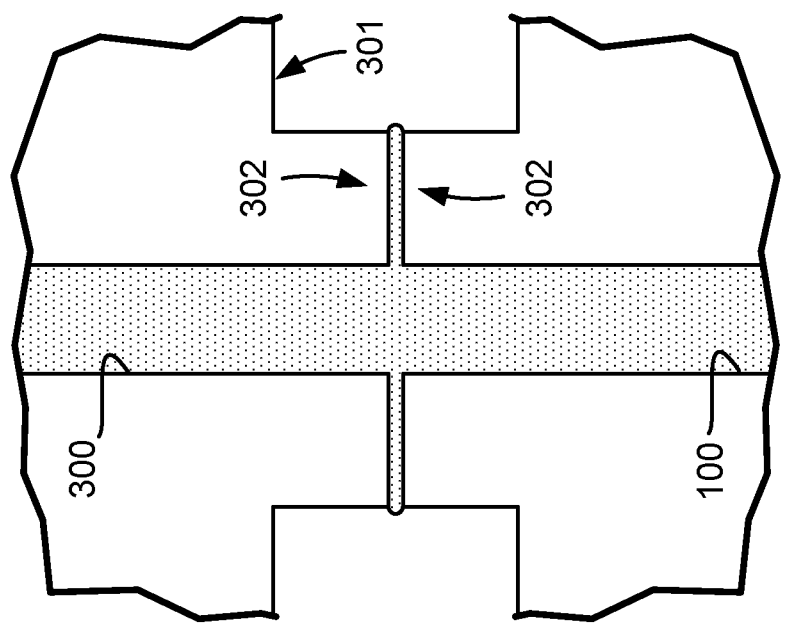
FIG. 3A is a further cross-sectional view of a modular microfluidic device in liquid communication, according to an exemplary embodiment.

A surprising advantage of the present invention is illustrated in FIG. 3. When two components having collars, 100 and 300, are placed in liquid communication with each other, there may be a natural tendency for the liquid (which is depicted by the hashing) to be drawn between the face of component 100 and component 300 by capillary forces. With the presence of the collar, the liquid may partially wet the outer sidewall and be pinned by the surface tension of the liquid. The placement of an abrupt larger gap 301 prevents and fluid that has seeped between the two smaller gap 302 from escaping the confined space even when a small amount of fluid has begun to wet the outside of the collar 303. This advantageously prevents the liquid from completely seeping between the components of the microfluidic device and results in long-term stability of the interface between components as well as enables repeated assembly and disassembly of components in the device while maintaining a fluid interface.

In some embodiments, the liquid within the channel suspends cells. In other embodiments, the second liquid within the second channel suspends cells. In certain embodiments, the liquid and the second liquid both suspend cells.

Another aspect of the invention are components for a modular microfluidic device comprising (a) a channel comprising an apex opening and (b) a structural tip in or near the apex opening, wherein the apex opening is at least partially surrounded by a collar configured to pin a liquid within the channel and wherein the pin is configured to allow for the flow of the liquid into the channel from a second component for a modular microfluidic device when the component is engaged with the second component.

The collar may comprise a channel sidewall, a face, and an outer sidewall, wherein the channel sidewall and the face define a first collar angle and wherein the face and the outer sidewall define a second collar angle.

The collar may comprise any suitable a collar material that allows for the pinning of a liquid within the component. The first angle may be greater than the contact angle of the liquid disposed on the collar material. The second angle is greater than the contact angle of the liquid disposed on the collar material.

In some embodiments, the channel may be a closed channel. In other embodiments, the channel is an open channel.

The collar may have any suitable radium for a particular application. In some embodiments, wherein the collar has a width of about X to about Y between the channel sidewall and the outer sidewall.

Figure 4:
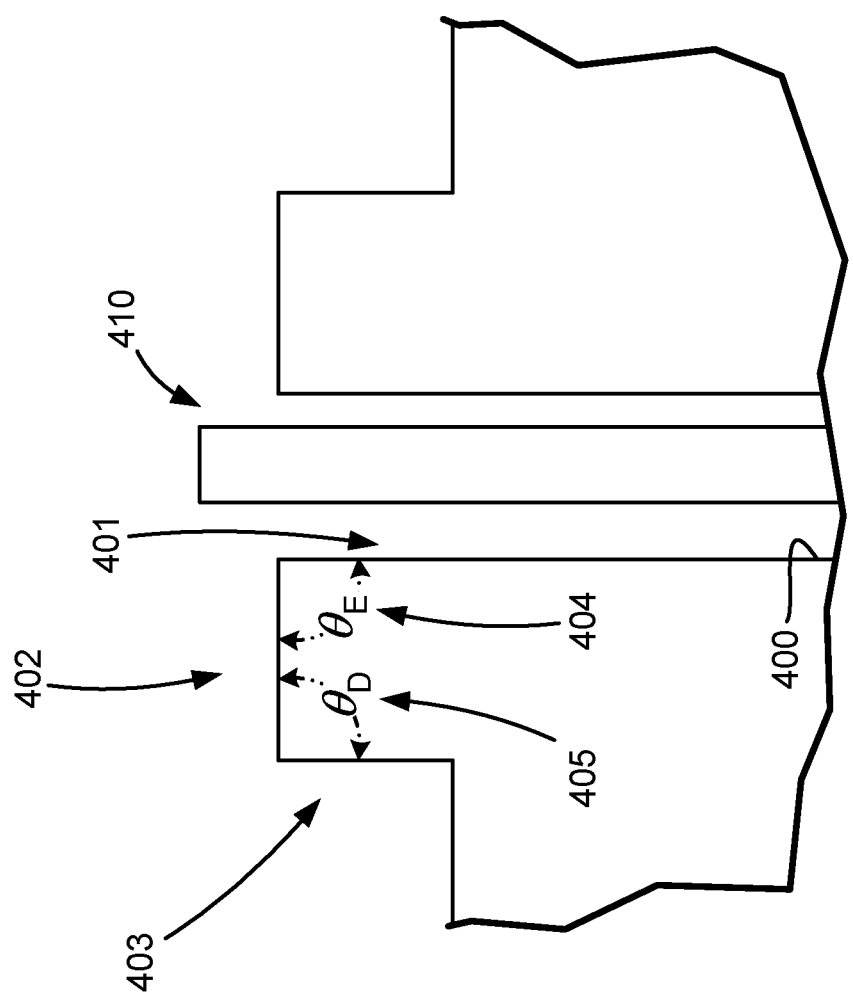
FIG. 4 is a further cross-sectional view of an exemplary pinning component in part of a modular microfluidic device, according to an exemplary embodiment.

FIG. 4 partially illustrates a component 400 for use with a modular microfluidic device that has a structural tip 410. The collar generally extends the channel away from the surface of the component and allows for the pinning of liquid within the component when the component is isolated from other components. The collar comprises a channel sidewall 401, a face 402, and an outer sidewall 403. The channel sidewall 401 and the face 402 define a first angle 404. The face 402 and the outer sidewall 403 define a second angle.

In some embodiments, the collar is configured to allow for flow of the liquid within the channel to a second component for a modular microfluidic device when the component is engaged with the second component. When the component is engaged with a second component, the structure pin can break the surface of the liquid, which allows for flow of liquid from one component to another.

In some embodiments, the second component comprises a second channel comprising a second apex opening, wherein the second apex opening is at least partially surrounded by a second collar configured to pin a second liquid within the channel.

A surprising advantage of the present invention is illustrated in FIG. 5. When two components having collars, 400 and 500, are placed in liquid communication with each other, there may be a natural tendency for the liquid (which is depicted by the hashing) to be drawn between the face of component 400 and component 500 by capillary forces. With the presence of the collar, the liquid may partially wet the outer sidewall and be pinned by the surface tension of the liquid. This advantageously prevents the liquid from completely seeping between the components of the microfluidic device.

In some embodiments, the liquid within the channel suspends cells. In other embodiments, the second liquid within the second channel suspends cells. In certain embodiments, the liquid and the second liquid both suspend cells.

Another aspect of the invention are components for a modular microfluidic device comprising a channel comprising a first apex opening and a second apex opening, wherein the first apex opening is at least partially surrounded by a first collar configured to pin a liquid within the channel and wherein the second apex opening is at least partially surrounded by a second collar configured to pin a liquid within the channel.

Another aspect of the invention are components for a modular microfluidic device, the component comprising a channel comprising (a) a first apex opening and a first pin at or near the first apex opening 410, wherein the first apex opening is at least partially surrounded by a first collar configured to pin a liquid within the channel and wherein the first pin is configured to allow for the flow of the liquid into the channel from a second component for a modular microfluidic device when the component is engaged with the second component, and (b) a second apex opening, wherein the second apex opening is at least partially surrounded by a second collar configured to pin a liquid within the channel. Interfacing a stable droplet in component 500 with the pin 410 of component 400 enables a reliable disruption of the stability of the fluid droplet in the apex opening of component 500 and results in the combining of fluids between components 400 and 500. This configuration also can be used to enable flow from component 400 to 500.

Another aspect of the invention are components for a modular microfluidic device comprising a channel comprising (a) a first apex opening and a first pin at or near the first apex opening, wherein the first apex opening is at least partially surrounded by a first collar configured to pin a liquid within the channel and wherein the first pin is configured to allow for the flow of the liquid into the channel from a second component for a modular microfluidic device when the component is engaged with the second component, and (b) a second apex opening and a second pin at or near the second apex opening, herein the second apex opening is at least partially surrounded by a second collar configured to pin a liquid within the channel and wherein the second pin is configured to allow for the flow of the liquid into the channel from a third component for a modular microfluidic device when the component is engaged with the third component.

Another aspect of the invention are modular microfluidic devices comprising a member any of the components or combinations of components described above.

Another aspect of the invention are modular microfluidic devices comprising at least two components, whether the same component or different components, described above.

EXAMPLES

In the examples of FIGS. 6A and 6B, a stack 600 having a suspended connection allows multiple layers 602A, 602B, 602C to be stacked in the vertical direction while containing liquid 604 in the chamber (best shown generally at 606 in FIG. 6A) formed by the openings in the layers 602A, 602B, 602C. The pinning design provides stable interfaces that the layers 602A, 602B, 602C can be removed from the stack, as is shown in FIG. 6B, thereby allowing the separation of the liquid 604A, 604B, 602C amongst the separated layers 602A, 602B, 602C. It is understood that the separation and stacking process is repeatable. Contained in the center chamber can be any form of liquid, not limited to water or organic solvent, or hydrogel.

Figure 7D:
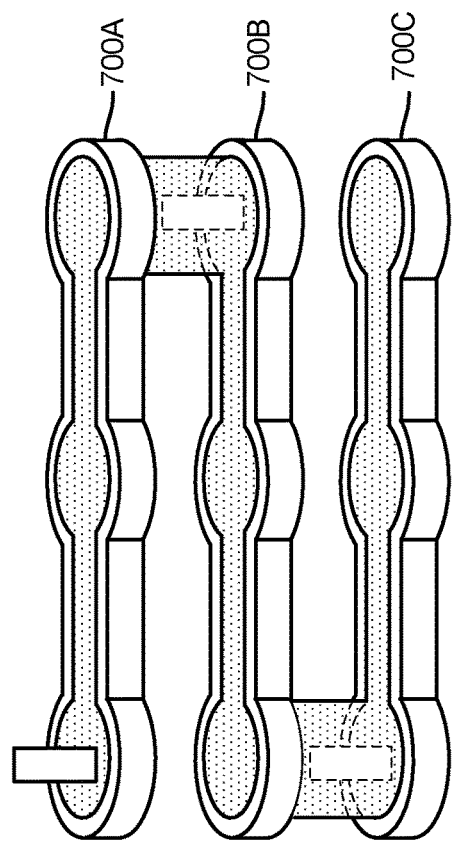
FIG. 7D is a perspective view of a flow channel, according to yet another exemplary embodiment.
Figure 7A:
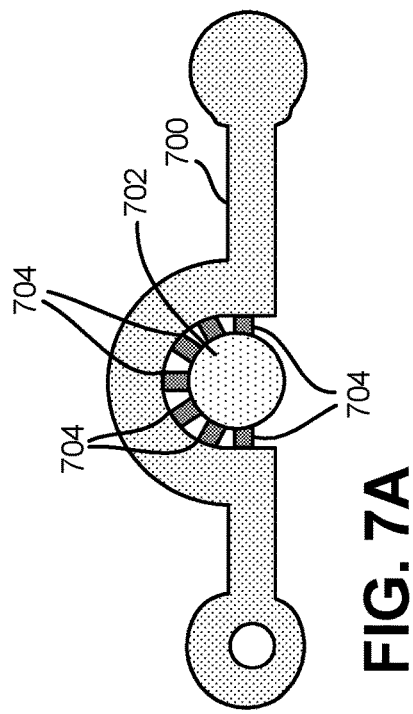
FIG. 7A is a top view of one embodiment of a flow channel, according to exemplary embodiments.
Figure 7B:
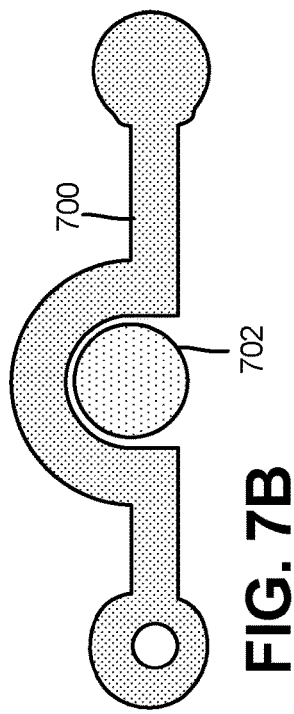
FIG. 7B is a top view of one embodiment of a flow channel, according to alternate exemplary embodiments.
Figure 7C:
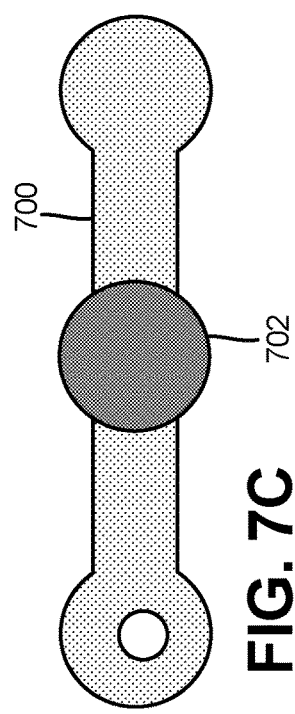
FIG. 7C is a top view of one embodiment of a flow channel, according to alternate exemplary embodiments.

In the examples of FIGS. 7A-7D, flow channels can be implemented to the culture chambers. FIG. 7A shows a channel 700 that is connected with a culture chamber 702 through diffusion pores 704. FIG. 7B depicts an example wherein a separate culture well 702 is separate from the flow channel 700. FIG. 7C represents a design where the entire area of the culture well 702 is covered with the flow channel 700. Flow through this example will replace all of the liquid in the culture chamber 702.

Each channel has suspended input and output described above. Alternating the position of the input and output allows stacking up channels 700A, 700B, 700C in the vertical direction to form a continuous flow path, as is shown in the example of FIG. 7D.

FIGS. 8A-8D depict further examples showing flow between modular devices, by showing the reversible connection between two modular devices 800A, 800B. In FIG. 8A, fluid is pinned 801 in open channel by surface tension in top device while bottom device is empty, where a pinning disruptor is found on top of second device (shown generally at 802). In FIG. 8B, the top device interfaces with bottom device and disruption of fluid pinning occurs when the pinned fluid makes contact with the apex 802 of the bottom device allowing flow 803 into an open channel or receptor on the bottom device 800B. As is shown in FIG. 8C, once fluid makes contact with the open channel attached to the raised collar 805 on the second device it flows through the channel (shown at 804) and empties the top device 800A of fluid. In these implementations, the fluid is contained to the device by a raised collar 805 and a protrusion 806. As shown in the example of FIG. 8D, following flow, the two devices 800A, 800B may be separated.

Figure 9D:
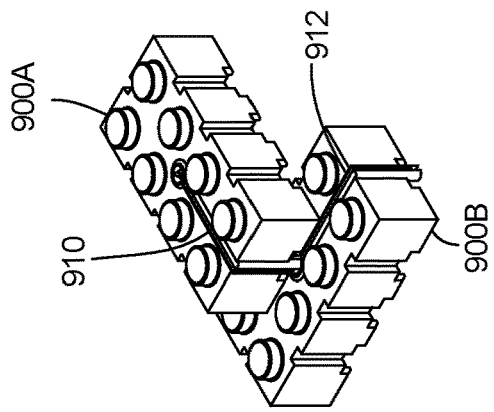
FIG. 9D is a perspective view of a peg-connected modular microfluidic devices, according to alternate embodiments.
Figure 9C:
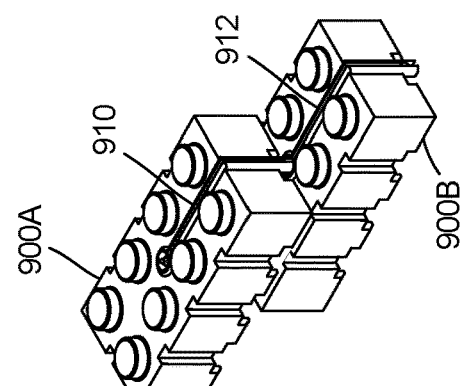
FIG. 9C is a perspective view of a peg-connected modular microfluidic devices, according to alternate embodiments.
Figure 9B:
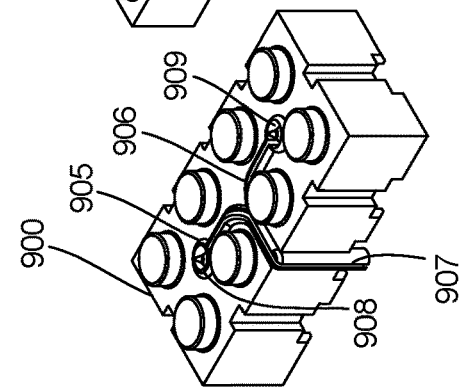
FIG. 9B is a perspective view of a peg-connected modular microfluidic device, according to alternate embodiments.
Figure 9A:
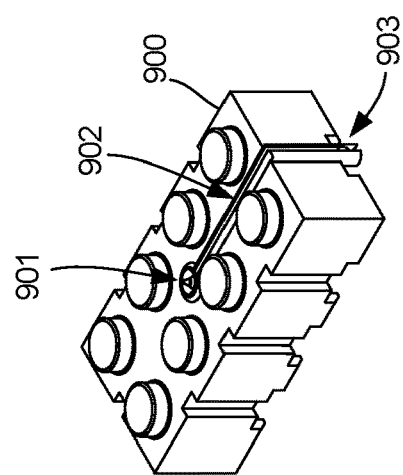
FIG. 9A is a perspective view of a peg-connected modular microfluidic device, according to exemplary embodiments.

FIGS. 9A-9D depict a peg connecting embodiment of modular connecting open microfluidic devices. In FIG. 9A, a straight open channel 902 design on surface of a connecting block 900 is shown. In this implementation, fluid can flow from a first position apex opening 901 to a second position 903, as has been previously described. In FIG. 9B, functional open microfluidic channels can be achieved, such that first 905 and second 906 channels are joined in a single channel 907. Adding two fluid pinning disruptor features 908, 909 to this device 900 thereby allows two devices (not shown) to be connected to same block 900 and output as single fluid (shown at 907). As shown in FIGS. 9C and 9D, two devices 900A, 900B are interfaced through peg connection and can be interfaced in multiple orientations such that flow is possible between the first device channel 910 and second device channel 912.

Other embodiments of modular microfluidic systems can allow the connection between 2 microfluidic layers without convective fluid flow. Connections allowing diffusive exchange between 2 layers can be designed. FIGS. 10A-I depict variations of liquid connection of modular open microfluidic devices for different modes of diffusive connections. In FIG. 10A, an suspended chamber was used to contain liquid or hydrogel 1001. This embodiment allows direct gel/liquid contact and diffusion. FIG. 10B represents a layer with solid bottom (shaded area) 1002. This embodiment prevents vertical liquid connection with the beneath layers. FIG. 10C represents a layer with solid bottom where pores are designed. The number and size of the pores can be varied. FIG. 10D-I depicts a liquid exchange process controlled by the size of pore 1003A. Large pores 1003B allow more liquid to drain to the bottom layer (FIG. 10G) during the separation. Consequently less liquid was remained in the top layer 1005A. Smaller pores 1003C, allows more liquid to be preserved in the upper layer 1005B during separation as in FIG. 10H,I.

Other functional designs are possible and fully within the scope of the invention, such as those described in U.S. Provisional Application No. 62/291,077 filed Feb. 4, 2016 and entitled "Modular Microfluidic Devices," which was incorporated by reference.

Robust Reconfigurable Cell-Based 3D Migration & Invasion Assay

We have leveraged the versatility of the stacks platform to design and develop a migration and invasion assay. The device consists of three stacks layers (FIG. 14A) with cylindrical wells that are assembled vertically to act as a single long well. The well is filled with collagen or other extracellular matrix protein. The bottom layer of the assembly contains a compound or other cell type that will generate a compound. Cell are placed on top of the top channel and incubated to allow migration following a gradient generated by the presence of the compound. Following incubation, the stack can disassembled with a small blade or wire cutter to precisely separate the layers and analyzed to determine the fraction of cells responsive to the compound and the speed at which they migrated.

Although the disclosure has been described with reference to preferred embodiments, persons skilled in the art will recognize that changes may be made in form and detail without departing from the spirit and scope of the disclosed apparatus, systems and methods.

What is claimed is:

1. An interconnecting block for a modular microfluidic network comprising:
   (a) a channel defined in the interconnecting block, the channel comprising an apex opening;
   (b) a collar at least partially surrounding an apex opening of a channel, the collar comprising a channel sidewall, a face, and an outer sidewall, wherein:
   (a) the channel sidewall and the face define a first collar angle and wherein the face and the outer sidewall define a second collar angle,
   (b) the collar is configured to pin a liquid within the channel, and
   (c) the interconnecting block is constructed and arranged to couple to a second interconnecting block via a peg connection so as to be in fluidic communication.

2. The component of claim 1, wherein the first collar angle is greater than or equal to the contact angle of liquid disposed on the collar.

3. The component of claim 2, wherein the second collar angle is greater than or equal to the contact angle of liquid disposed on the collar.

4. The component of claim 1, wherein the channel has a channel length of about 1 mm to about 100 mm.

5. The component of claim 1, wherein the channel has a mean radius of about 100 μm to about 2 mm.

6. The component of claim 1, wherein the channel has a channel volume of about 100 nL to about 300 μL.

7. The component of claim 1, wherein the channel is a closed channel or an open channel.

8. The component of claim 1, wherein the collar has a width of about 100 μm to about 2 mm.

9. The component of claim 1, wherein:
   (i) the collar is configured to allow for flow of the liquid within the channel to a second component for a modular microfluidic device when the component is engaged with a second component;
   (ii) the collar is configured to allow for diffusion of the liquid within the channel to a second component for a modular microfluidic device when the component is engaged with the second component; or
   (iii) both (i) and (ii).

10. The component of claim 9, wherein the second component comprises a second channel comprising a second apex opening, wherein the second apex opening is at least partially surrounded by a second collar configured to pin a second liquid within the channel.

11. The component of claim 1, wherein (i) the liquid within the channel suspends cells, (ii) the second liquid within the second channel suspends cells, or both (i) and (ii).

12. A interconnecting modular microfluidic device comprising:
   (a) a channel comprising a collar and an apex opening; and
   (b) a structural tip in or near the apex opening, wherein the collar comprises a channel sidewall, a face, and an outer sidewall,
   wherein the channel sidewall and the face define a first collar angle and wherein the face and the outer sidewall define a second collar angle,
   wherein the apex opening is at least partially surrounded by a collar configured to pin a liquid within the channel,
   wherein the pin is configured to allow for the flow of the liquid into the channel from a second interconnecting modular microfluidic device when the component is engaged with the second component via a peg connection.

13. The component of any of claim 12, wherein the first collar angle is greater than or equal to the contact angle of the liquid disposed on the collar.

14. The component of any of claim 13, wherein a second collar angle is greater than or equal to the contact angle of the liquid disposed on the collar.

15. The component of any of claim 12, wherein the channel has a channel length of about 1 mm to about 100 mm.

16. A modular medical device network, comprising one or more modular components, each modular component comprising:
   (a) a first interconnecting block comprising at least one first block channel comprising a first apex opening comprising a first collar constructed and arranged to pin liquid therein via surface tension; and
   (b) a second interconnecting block comprising at least one second block channel comprising a second apex opening comprising a second collar constructed and arranged to pin liquid therein via surface tension,
   wherein the first and second interconnecting blocks can be joined via a peg connection so as to be in fluidic communication.

17. The modular medical device network of claim 16, wherein the second interconnecting block further comprises at least one protrusion constructed and arranged to extend into a fluidic path defined by the first interconnecting block.

18. The modular medical device network of claim 16, wherein:
   (i) the second collar is configured to allow for flow of the liquid within the first channel to the second channel,
   (ii) the first collar is configured to allow for diffusion of liquid within the first channel to the second channel, or
   (iii) both (i) and (ii).

* * * * *